(12) United States Patent
Leifenberg (10) Patent No.: US 12,156,677 B2
(45) Date of Patent: Dec. 3, 2024

(54) DEVICE AND METHOD FOR CLEARING AN OBSTRUCTED AIRWAY

(71) Applicant: EXTRALIFE LTD., Tel-Aviv-Yafo (IL)

(72) Inventor: Yaron Leifenberg, Tel-Aviv (IL)

( * ) Notice: Subject to any disclaimer, the term of this patent is extended or adjusted under 35 U.S.C. 154(b) by 155 days.

(21) Appl. No.: 17/976,910

(22) Filed: Oct. 31, 2022

(65) Prior Publication Data
US 2023/0053877 A1 Feb. 23, 2023

Related U.S. Application Data (63) Continuation of application No. 17/251,832, filed as application No. PCT/IL2019/050673 on Jun. 14, 2019, now Pat. No. 11,484,343.

(60) Provisional application No. 62/684,805, filed on Jun. 14, 2018.

(51) Int. Cl.
*A61B 17/50* (2006.01)
*A61B 17/24* (2006.01)
*A61M 1/00* (2006.01)

(52) U.S. Cl.
CPC .............. *A61B 17/50* (2013.01); *A61B 17/24* (2013.01); *A61M 1/81* (2021.05)

(58) Field of Classification Search
CPC ... A61B 17/50; A61B 17/24; A61B 2017/306; A61M 1/81; A61M 1/67; A61M 1/74; A61D 1/12
See application file for complete search history.

(56) References Cited

U.S. PATENT DOCUMENTS

| | | | | |
|---|---|---|---|---|
| 4,971,053 A | * | 11/1990 | Tarrats | A61B 17/50 128/206.28 |
| 2011/0160683 A1 | * | 6/2011 | Pinotti Barbosa | A61M 1/732 604/319 |
| 2014/0276498 A1 | * | 9/2014 | Connor | A61M 1/67 604/321 |
| 2016/0174956 A1 | * | 6/2016 | Ciulla | A61B 17/221 606/1 |

OTHER PUBLICATIONS

Education.com, "Hooke's Law: Calculating Spring Constants". https://www.education.com/science-fair/article/springs-pulling-harder/ (Year: 2011).*

* cited by examiner

*Primary Examiner* — Sarah W Aleman
*Assistant Examiner* — Mikail A Mannan
(74) *Attorney, Agent, or Firm* — AlphaPatent Associates Ltd.; Daniel J. Swirsky (57) ABSTRACT

A device for clearing an obstructed airway of a subject, including an airway interface configured to be positioned over a mouth and/or nose of the subject, a pump in fluid communication with the airway interface and configured to generate suction at the airway interface when activated, and a sleeve surrounding the pump, where the device is configured to activate the pump to generate the suction when the airway interface is pushed against the mouth and/or nose of the subject by pushing on the sleeve, where the device is configured to be held and activated with one hand.

14 Claims, 10 Drawing Sheets

DEVICE AND METHOD FOR CLEARING AN OBSTRUCTED AIRWAY

FIELD

The present disclosure relates to a device for clearing an obstructed airway to methods of using same and, more particularly, to a device capable of generating suction in an airway when positioned over a mouth and/or nose of a subject and pressed thereagainst.

BACKGROUND

Choking due to an obstructed airway is a leading cause of accidental death. One type of aid for choking subjects is abdominal thrusts (also called the Heimlich maneuver) a procedure in which pressure is exerted on the bottom of the diaphragm of the choking subject to compress the lungs and force out any object lodged in the airway (typically trachea).

Devices designed for generating low pressure or a vacuum in an airway above the obstruction to thereby suction and dislodge an object lodged in a person's airway are known in the art. Such devices typically employ manual mechanisms for creating and/or applying suction to an airway of a choking subject. While such devices can be effective in clearing obstructions they typically require several operational steps to create and apply suction and thus it would be difficult for the choking subject to self-operate such devices or for persons providing assistance to operate on infants or subjects. Some devices require repeated pumping of the vacuum mechanism, making operation more complex and also resulting in more complex devices that require one-way valves since the device is being "reset" while in position on the subject.

For example, the LifeVac manufactured by LifeVac LLC of Nesconset, NY is a manual suction device for resuscitating choking subjects that includes a suction bulb connected to an airway mask via a one way valve. When utilized on a choking subject, the LifeVac device creates a one-way suction force to dislodge any food or object lodged in the airway. Although the LifeVac device can be used to dislodge objects present in an airway it requires manual suctioning using both hands and would be difficult to either self-operate or operate on a patient that requires additional assistance such as an infant, when choking.

There is thus a need for, and it would be highly advantageous to have, an airway clearing device that can be easily and quickly operated by the choking subject and/or persons administering first aid to the choking subject.

The description above is presented as a general overview of related art in this field and should not be construed as an admission that any of the information it contains constitutes prior art against the present patent application.

SUMMARY

The present disclosure is of a device for clearing obstructed airways which can be used to treat choking subjects (as an anti-choking device). Specifically, the present disclosure is configured such that it can be used by a single hand and thus enables the choking subject to self-clear an obstruction in an airway (e.g. tracheal blockage) or allow a person lending assistance to use one hand to support the subject while the other hand operates the device. The device as presented herein has the following advantageous features:
  (i) does not require a series of steps to operate and/or apply suction to an airway;
  (ii) can be used by the choking subject to self-administer suction;
  (iii) simple and reliable construction with no need for one-way valves;
  (iv) can be disposed of after single use or used repeatedly;
  (v) can accommodate both adults and children;
  (vi) can be operated with a single hand leaving a free hand to support the head of the subject etc.; and
  (vii) can be reset for additional use.

Thus, according to one aspect of the present disclosure there is provided device that can be used to clear an airway obstruction in a human subject such as a choking subject. The present device includes a source of suction (also referred to herein as pump) that is activated to generate suction at an airway interface (e.g. airway mask that covers the mouth and/or nose). The present device also includes a mechanism for activating such suction when the airway interface is pressed against the airway opening, e.g., pressed against the skin surrounding the mouth and/or nose.

Such automatic activation of suction is advantageous in that it does not require the user (e.g. choking subject or person lending assistance) to manually generate the suction force (via manual pumping or by flipping a switch to activate pumping) or to trigger application of suction to the airway. It also ensures that suction is only applied when the device is sealed around the airway opening.

According to some embodiments of the present disclosure, a device for clearing an obstructed airway of a subject comprises: an airway interface adapted for positioning over a mouth and/or nose of the subject; and a pump in fluid communication with the airway interface and being activatable to generate suction at the airway interface, wherein the device is adapted for activation of the pump to generate the suction when the airway interface is pushed against the mouth and/or nose of the subject. In some embodiments, the pump comprises a spring and a piston both mounted in a cylinder, adapted such that the spring is compressed when the piston is locked in a closed position and adapted such that unlocking of the piston results in decompression of the spring for the activation of the pump.

In some embodiments, the device further comprises a body comprising a grippable sleeve slidably mounted on the cylinder for pushing the airway interface against a mouth and/or nose of a subject and adapted to unlock the piston by the pushing of the sleeve. In some embodiments, the device is adapted to be held and activated with one hand. In some embodiments, the device further comprises a lock pin adapted to hold the piston in a locked position.

In some embodiments, the body further comprises a slanted grove and the cylinder further comprises an L-shaped groove comprising a locked part for holding the lock pin in a locked position, the device adapted such that movement of the body towards the airway interface caused by pushing the grippable sleeve, moves the slanted groove to thereby drive the lock pin along the slanted groove to thereby move the lock pin into an unlocked part of the L-shaped groove to thereby unlock the piston.

In some embodiments, the airway interface includes a seal for sealing around a mouth and/or nose of a subject. In some embodiments, a spring constant of the spring is 200-400 N/m. In some embodiments, a force applied by the spring is 50-90 N. In some embodiments, the pump is capable of generating a suction force greater than 100 mm Hg within a second or less. In some embodiments, the pump includes a pneumatic/hydraulic piston.

In some embodiments, a method of clearing an obstructed airway comprises positioning the device disclosed above over a mouth and/or nose of a subject and pushing the airway interface against the mouth and/or nose to thereby activate the pump and clear the obstructed airway. In some embodiments, the device further comprises a release lever to for unlocking the piston.

According to other aspects of the present disclosure there is provided a device for clearing an obstructed airway of a subject comprising a device body including a pump being activatable to generate suction at an airway interface configured for positioning over a mouth and/or nose of the subject, wherein the pump is activated to generate suction when the airway interface is pushed against the mouth and/or nose.

According to embodiments of the disclosure the pump includes a spring-loaded piston.

According to embodiments of the disclosure the spring is released when the airway interface is pushed against the mouth and/or nose.

According to embodiments of the disclosure pushing the airway interface against the mouth and/or nose releases a lock pin locking the piston in position.

According to embodiments of the disclosure the airway interface moves relative to the device body when pushed against the mouth and/or nose.

According to embodiments of the disclosure the airway interface includes a seal for sealing around the mouth and/or nose.

According to embodiments of the disclosure a spring constant of the spring is 200-400 N/m.

According to embodiments of the disclosure a force applied by the spring is 50-90 N.

According to embodiments of the disclosure a displacement of the spring is 50-150 mm.

According to another aspect of the present disclosure there is provided a method of clearing an obstructed airway comprising positioning the device over a mouth and/or nose of a subject and pushing/pressing the airway interface against the mouth and/or nose to thereby activate the pump and clear the obstructed airway.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The disclosure is herein described, by way of example only, with reference to the accompanying drawings. With specific reference now to the drawings in detail, it is stressed that the particulars shown are by way of example and for purposes of illustrative discussion of the preferred embodiments of the present disclosure only, and are presented in the cause of providing what is believed to be the most useful and readily understood description of the principles and conceptual aspects of the disclosure. In this regard, no attempt is made to show structural details of the disclosure in more detail than is necessary for a fundamental understanding of the disclosure, the description taken with the drawings making apparent to those skilled in the art how the several forms of the disclosure may be embodied in practice.

In the drawings.

DETAILED DESCRIPTION

The present disclosure is of a device for clearing obstructed airways which can be used to treat choking subjects (as an anti-choking device). The principles and operation of the present disclosure may be better understood with reference to the drawings and accompanying descriptions.

Before explaining at least one embodiment of the disclosure in detail, it is to be understood that the disclosure is not limited in its application to the details of construction and the arrangement of the components set forth in the following description or illustrated in the drawings. The disclosure is capable of other embodiments or of being practiced or carried out in various ways. Also, it is to be understood that the phraseology and terminology employed herein is for the purpose of description and should not be regarded as limiting.

Thus, according to one aspect of the present disclosure there is provided device that can be used to clear an airway obstruction in a human subject such as a choking subject.

The present device includes a source of suction (also referred to herein as pump) that is activated to generate suction at an airway interface (e.g. airway mask that covers the mouth and/or nose). The present device also includes a mechanism for activating such suction when the airway interface is pressed against the airway opening, e.g., pressed against the skin surrounding the mouth and/or nose.

Several types of pumps can be used by the present device including piston-type pumps, rotary pumps and the like; the pump can be mechanical or motor driven. Mechanical pumps can include spring, hydraulic or pneumatic driven pistons.

In some embodiments, the selected pump is capable of generating a suction force greater than 100 mm Hg within a second or less.

According to one embodiment of the present disclosure the pump is a spring loaded piston positioned in a cylinder. Such a configuration is advantageous in that it can rapidly generate the vacuum force necessary for dislodging (sucking out) an object in the airway of a subject when the spring is released. Release of the spring for activation of the piston is performed by pressing the airway interface (mask) against the skin around the nose and mouth of the choking subject thereby releasing a locking pin holding the spring in the loaded (compressed) position.

A more detailed description of this embodiment of the present device is provided hereinbelow with reference to FIGS. 1A-1I and FIG. 2.

Referring now to the drawings, FIGS. 1A-1I are illustrative drawings of a device for clearing an airway obstruction according to some embodiments. FIGS. 1A, 1C, 1E, 1G, and 1I show device 10 in a closed position, and FIGS. 1B, 1D, 1F, and 1H show device 10 in an open position. When device 10 is referred to as "closed herein, device 10 is ready for use on a subject. When device 10 is referred to herein as "open", device 10 is post-usage. FIGS. 1C-1I are cutaway or partial cutaway illustrations.

As shown, a device 10 includes a device body 12 covered with a graspable non-slip sleeve 13 (e.g., ridged silicone sleeve) and slidably surrounding a pump mechanism 14 that is activatable to generate suction at an airway interface 16 that is attached to pump mechanism 14.

In some embodiments, airway interface 16 is mask-like in shape (e.g. a pear-shaped cup) and includes an internal volume 26 defined by the walls of airway interface 16. The skin-contacting portion of airway interface 16 includes a seal 19 for sealing around the nose and mouth of a subject. In some embodiments, airway interface 16 is replaceable and is provided as part of a kit having two or more airway interface 16 sizes (e.g. sized to fit an adult or child). In some embodiments, dimensions for seal 19 are between 40-90 mm in width (across the face) and 40-110 mm in height.

In some embodiments, device body 12 and airway interface 16 are fabricated from an alloy and/or polymer using well known fabrication approaches (e.g. machining, injection molding, 3D printing and the like). In some embodiments, seal 19 is fabricated from rubber or silicon and fitted over a rim of airway interface 16.

As shown, pump mechanism 14 includes a spring 18 pressing against a piston 20 positioned in a cylinder 22. Spring 18 is shown in a compressed state in FIG. 1C and an uncompressed state in FIG. 1D. In some embodiments, spring 18 is fabricated from an alloy such as stainless steel. In some embodiments, spring 18 has a spring constant (K) of 200-400 N/m. In some embodiments, spring 18 has a diameter of 30-50 mm. In some embodiments, cylinder 22 is 40-60 mm in diameter and 100-150 mm in length.

Figure 1A:
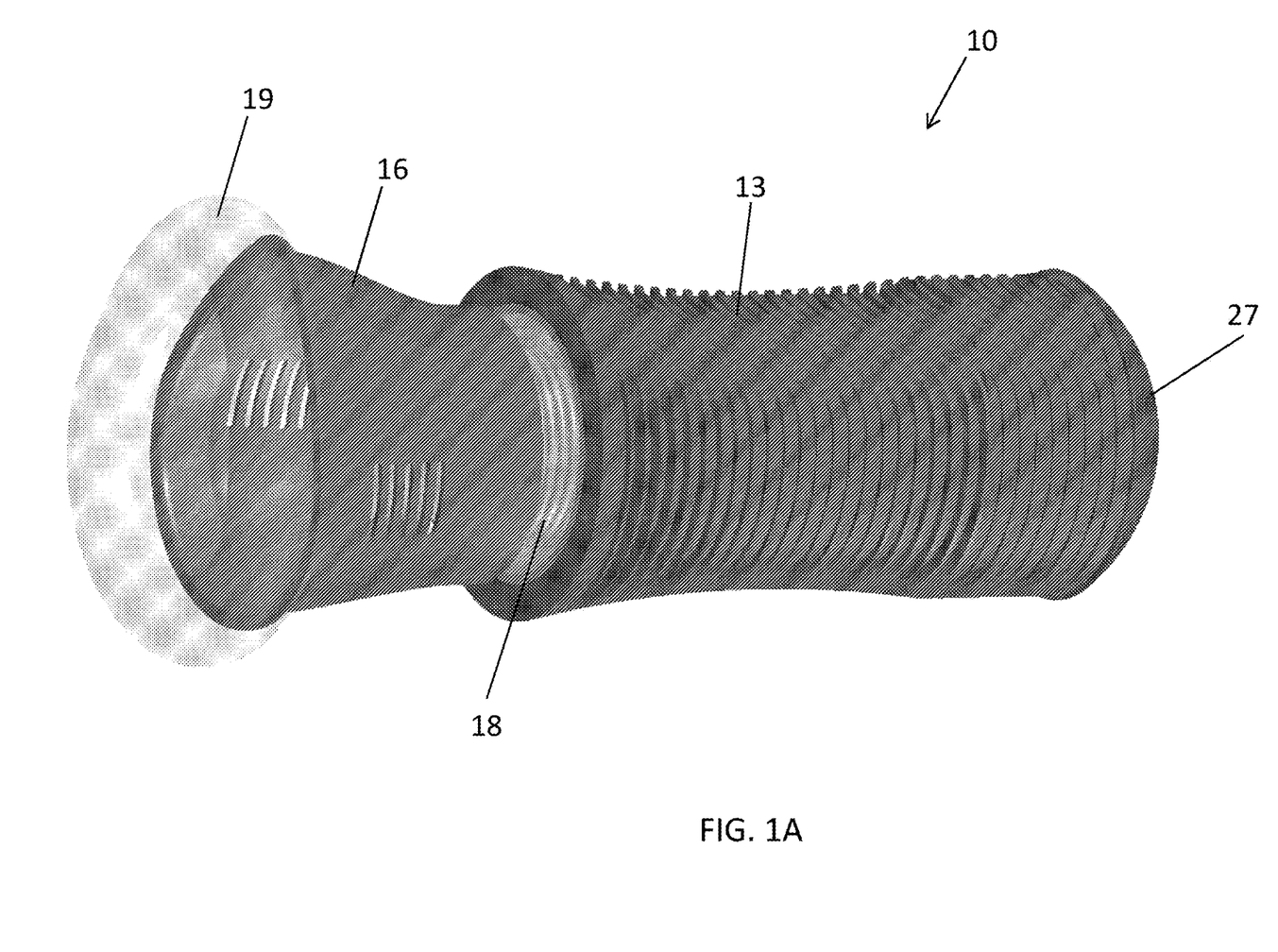
FIGS. 1A-1I are illustrative drawings of a device for clearing an airway obstruction according to some embodiments.
Figure 1B:
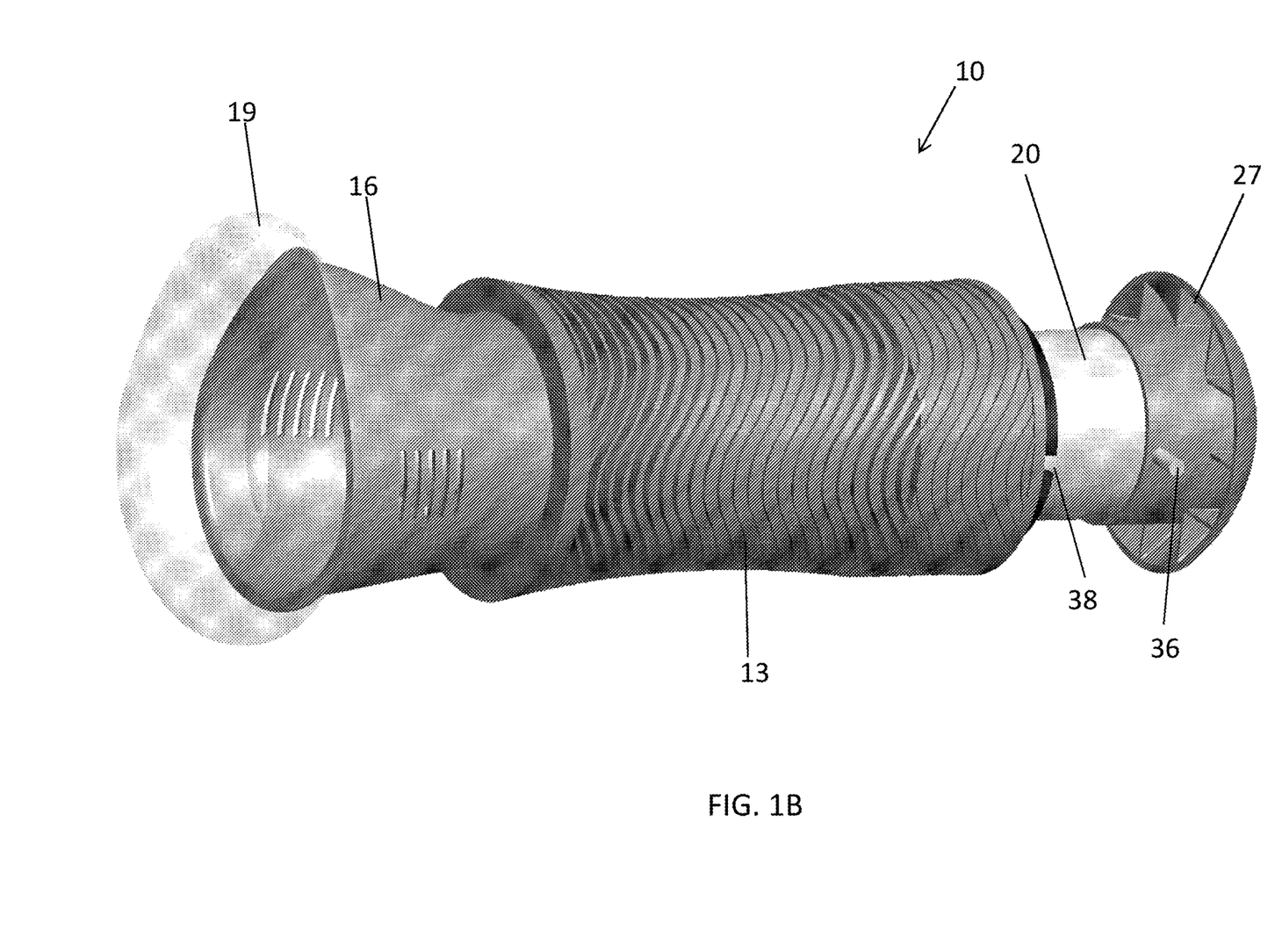
Figure 1C:
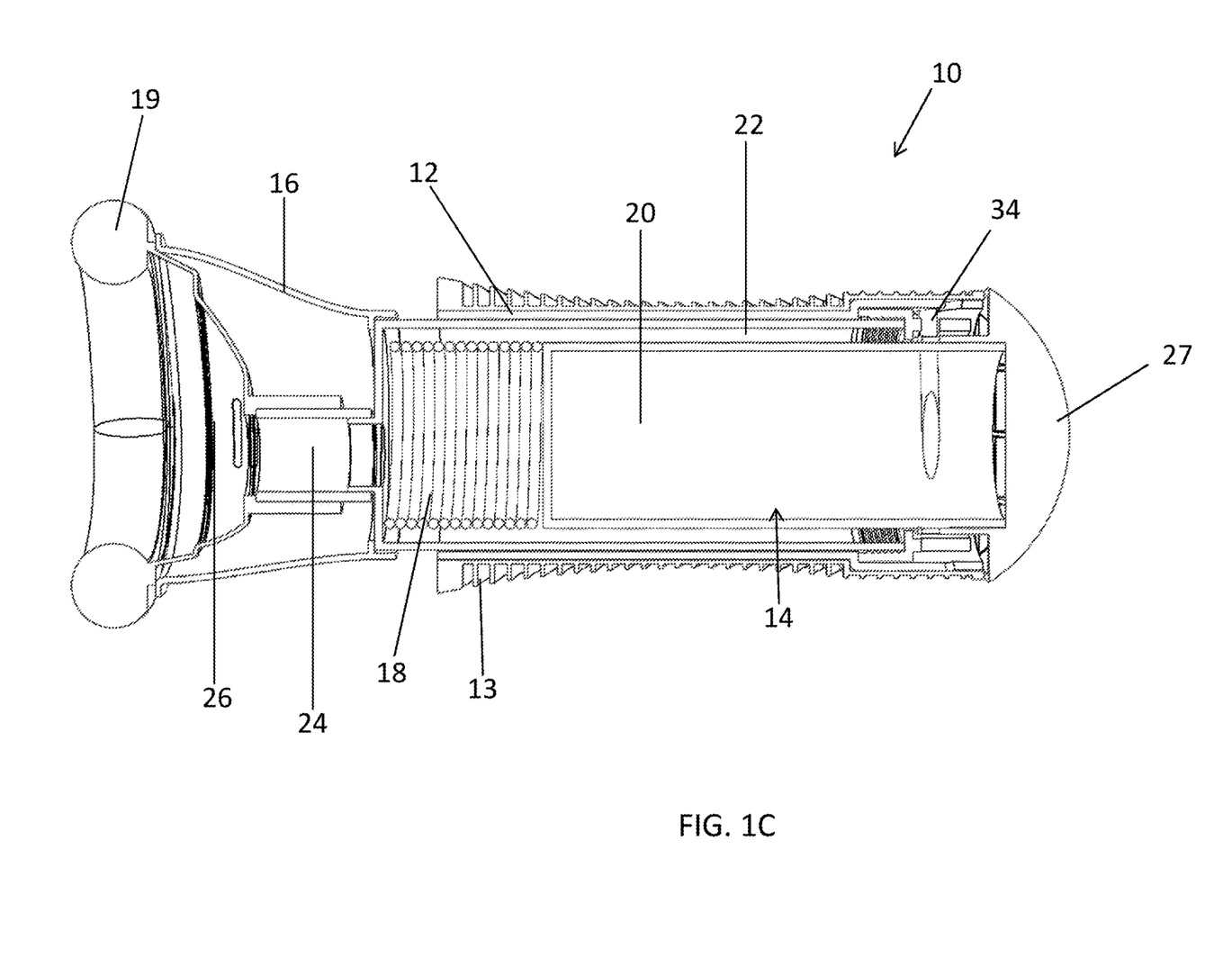
Figure 1D:
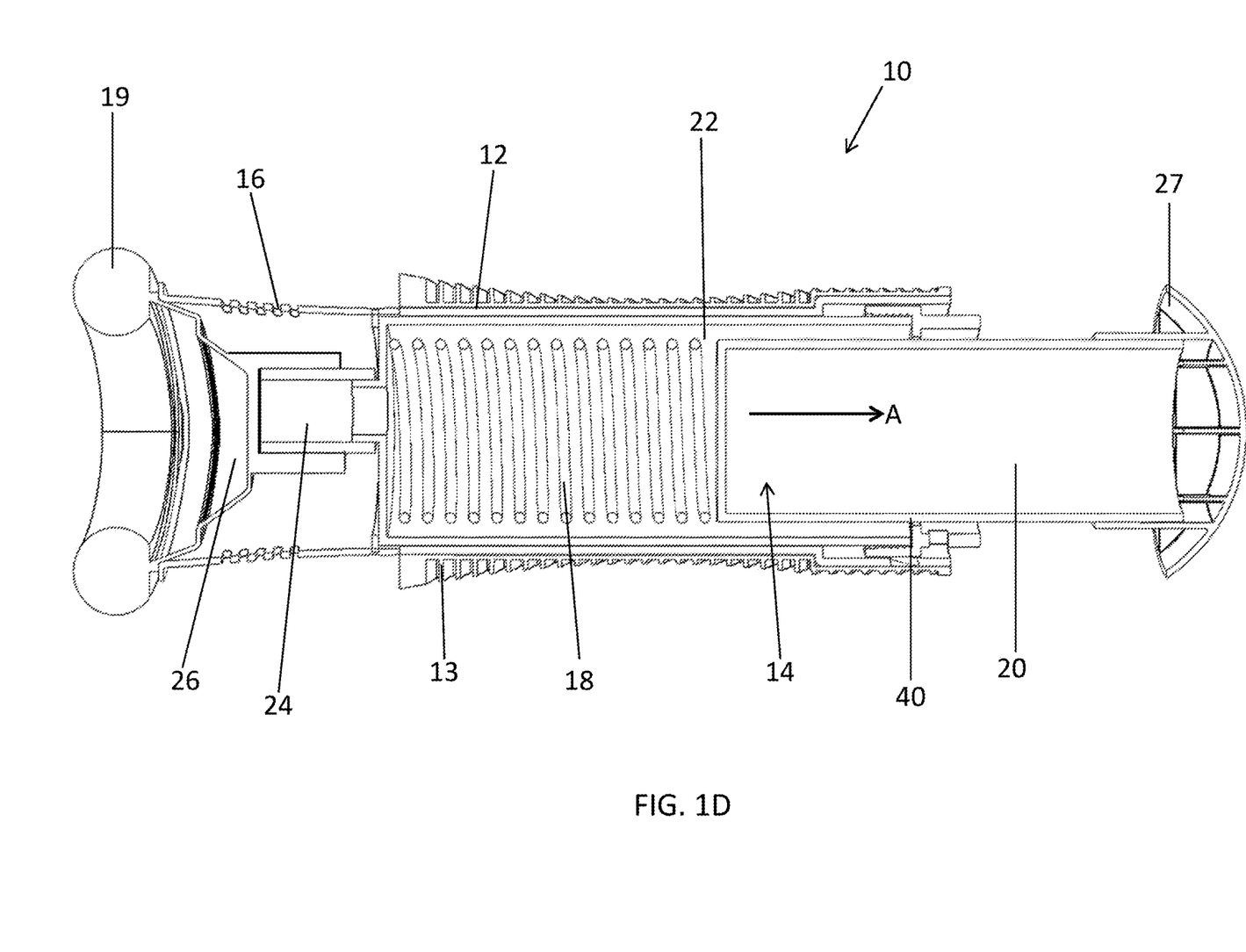
Figure 1E:
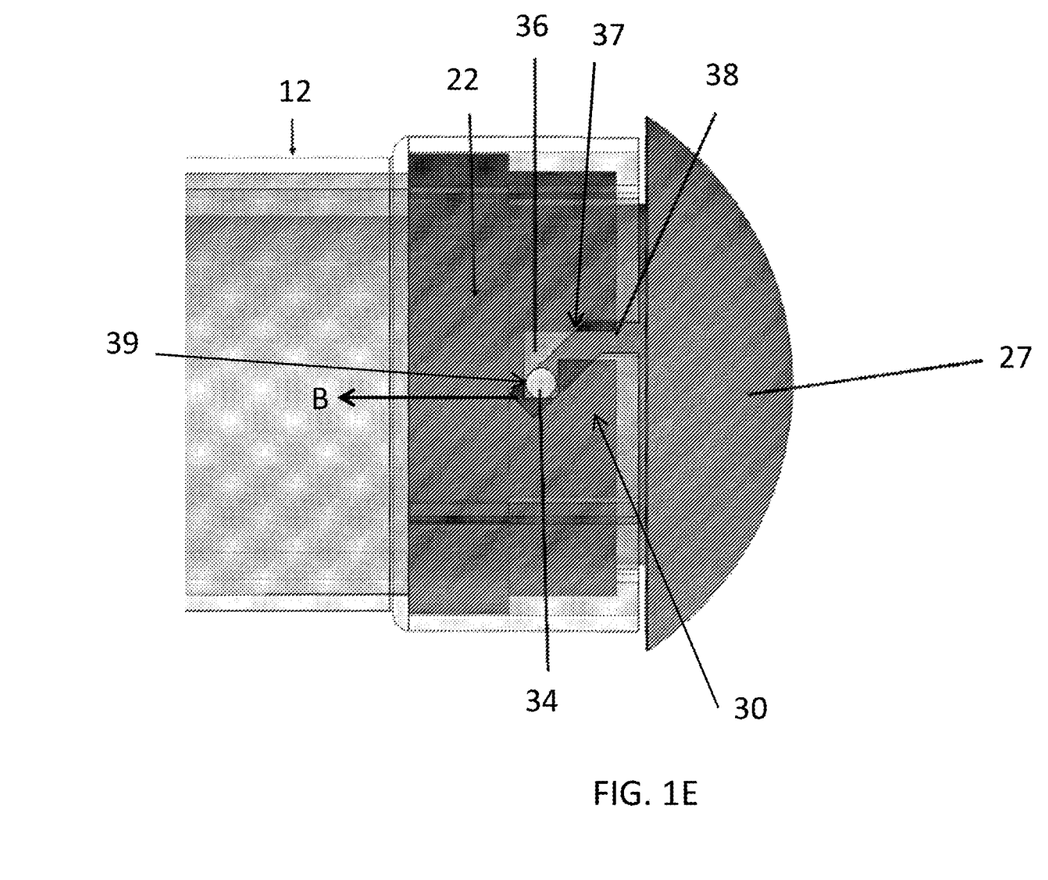
Figure 1F:
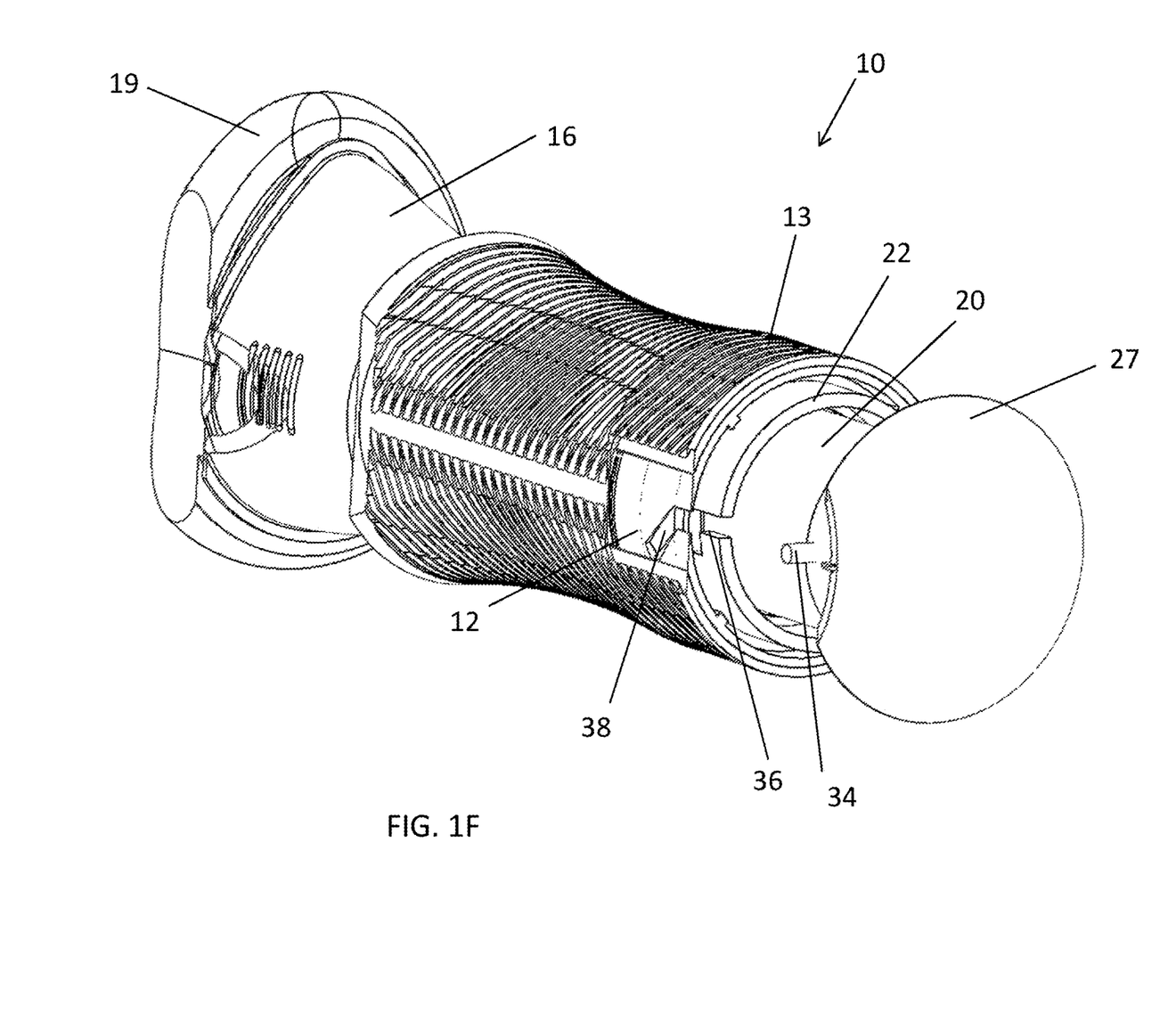
Figure 1G:
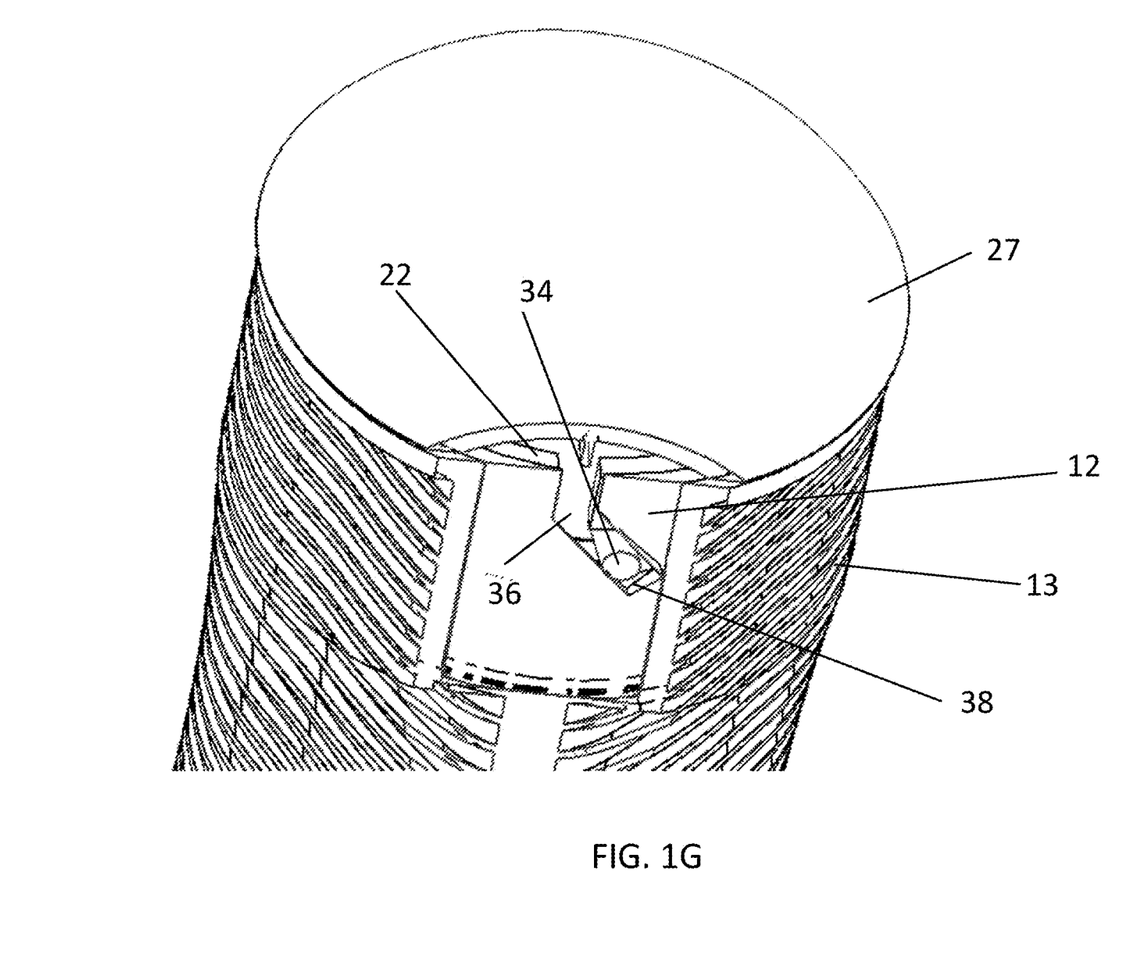

As shown, piston 20 is an elongated cylindrical body sealed against the walls of cylinder 22 and is slidable within cylinder 22. Body 12 is slidable over cylinder 22. When configured as an elongated cylindrical body as shown, piston 20 and attached distal cap 27 move outwards from cylinder 22 and away from device body 12 when spring 18 is triggered. In some embodiments, a seal 40 is positioned at the distal end of cylinder 22 for further enhancing the suction in cylinder 22 generated when piston 20 is activated.

In some embodiments, piston 20 is configured as a disc (not shown) and a pressure release valve (not shown) is provided at the distal end of device body 12 to release pressure buildup in cylinder 22 when the disc-like piston is released.

A cylinder-type piston 20 is advantageous in that it enables an operator to easily push the protruding end of the cylinder-type piston 20 back into device body 12 thereby compressing spring 18 and 'rearming' device 10 for repeated use.

Cylinder 22 is fluidly connected to internal volume 26 of airway interface 16 via conduit 24. Optionally conduit 24 is not used and cylinder 22 is directly fluidly connected to internal volume 26. When spring 18 is released, piston 20 moves in a direction opposite that of airway interface 16, as shown by arrow "A", to generate negative pressure in cylinder 22 which results in a suction force at internal volume 26 of airway interface 16 that results in a suction force from the airway of the subject when airway interface 16 is positioned over the airway of the subject.

As above, in some embodiments, release of spring 18 is triggered by pressing airway interface 16 (seal 19) against a surface such as skin surrounding the mouth and/or nose of a subject.

Figure 1H:
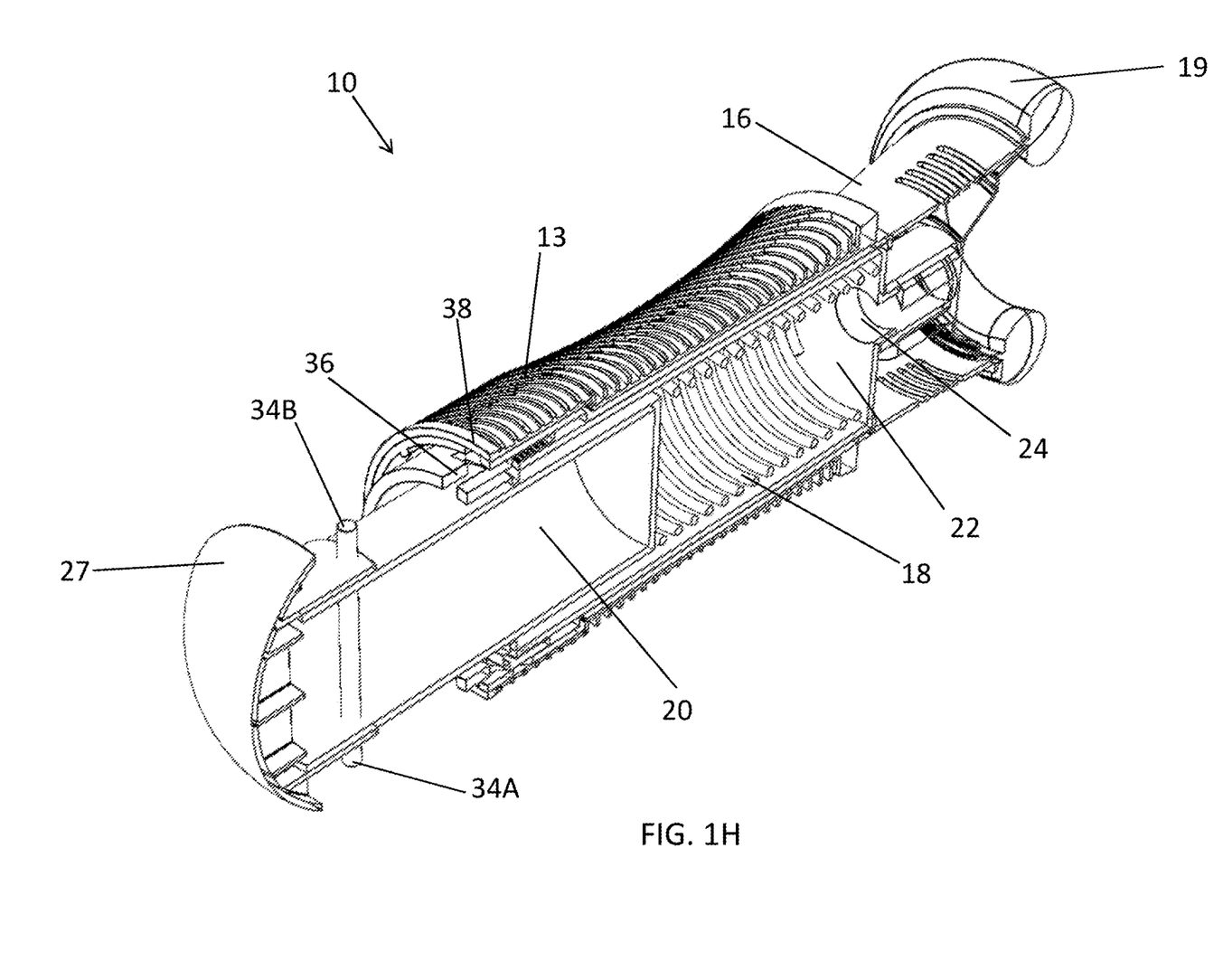

One embodiment of a triggering mechanism 30 is shown in FIGS. 1E-1I. Trigger mechanism 30 includes a lock pin 34 protruding from piston 20. When device 10 is closed, lock pin 34 is positioned within both of an L-shaped groove 36 in cylinder 22 and also a slanted groove 38 forming a part of body 12 to thereby lock piston 20 in a closed position inside cylinder 22. As shown, trigger mechanism 30 is duplicated on either side of device 10 (FIG. 1H). In some embodiments, trigger mechanism is provided on one side of device 10 only.

Figure 2:
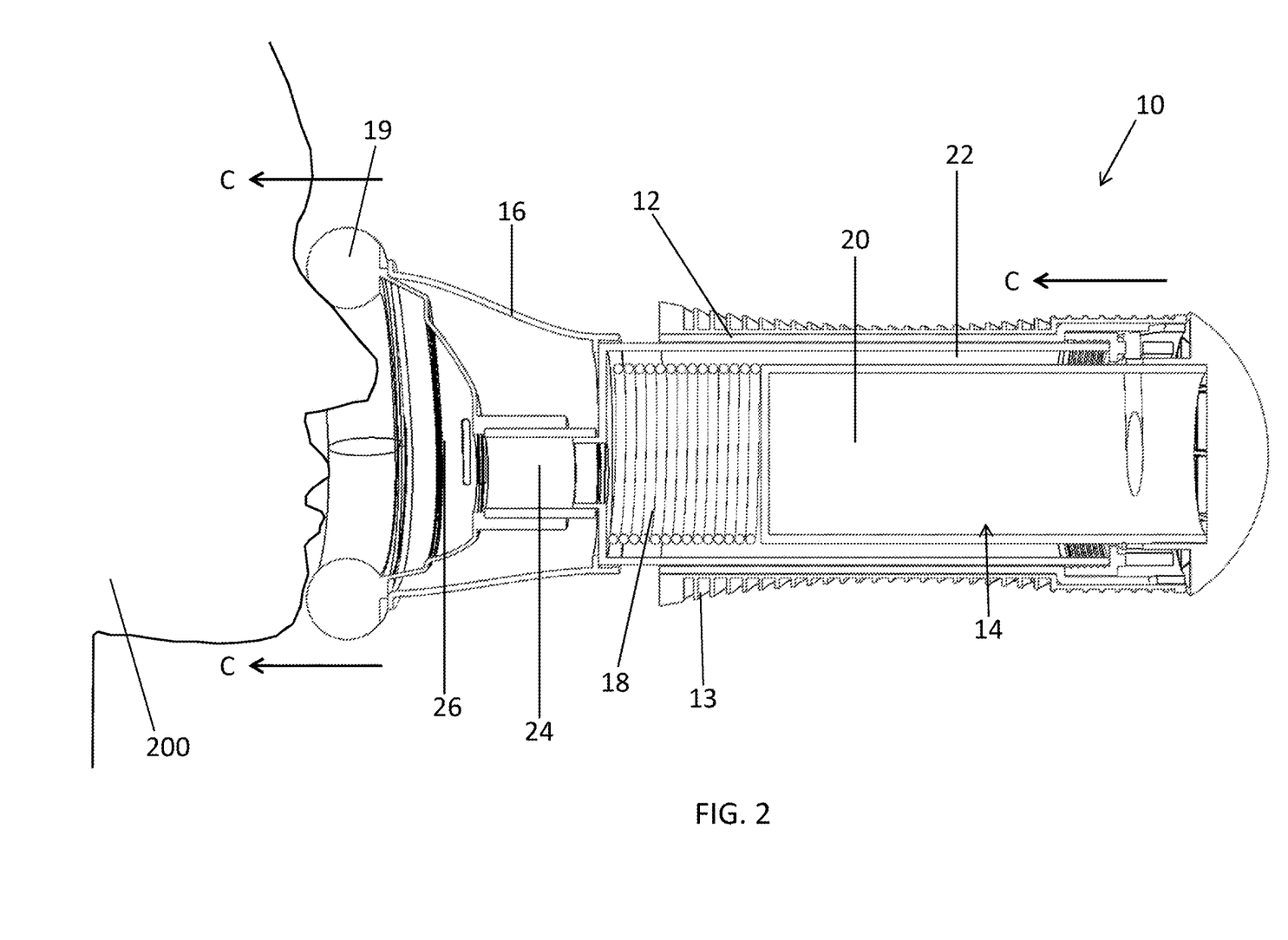
FIG. 2 shows an illustrative drawing of use of a device for clearing an airway obstruction according to some embodiments.

In use, seal 19 is forced (pressed) against a subject's airway opening by gripping sleeve 13 and pushing sleeve 13 towards the face of the subject in a direction "C" (FIG. 2). As a result, sleeve 13 and attached device body 12 are pushed towards airway interface 16. As device body 12 moves in direction "B", slanted groove 38 moves in direction B and twists lock pin 34 out of the locked part 39 of L-shaped groove 36 to the point of release of lock pin 34 in the perpendicular unlocked part 37 of L-shaped groove 36 thereby freeing piston 20 from cylinder 22. As a result, spring 18 is no longer held in a compressed position by piston 20 and spring 18 uncompresses and pushes piston 20 away from airway interface 16 within cylinder 22 to thereby generate negative pressure within cylinder 22 and resulting negative pressure in internal volume 26 and thus also in the airway of the subject for sucking out an airway blockage. In some embodiments, the friction of movement of body 12 over cylinder 22 is increased to thereby require harder pressing using sleeve 13 to activate device 10 to thereby force seal 19 into optimum contact with the face of the subject and prevent activation of device 10 until a complete seal is formed.

Figure 1I:
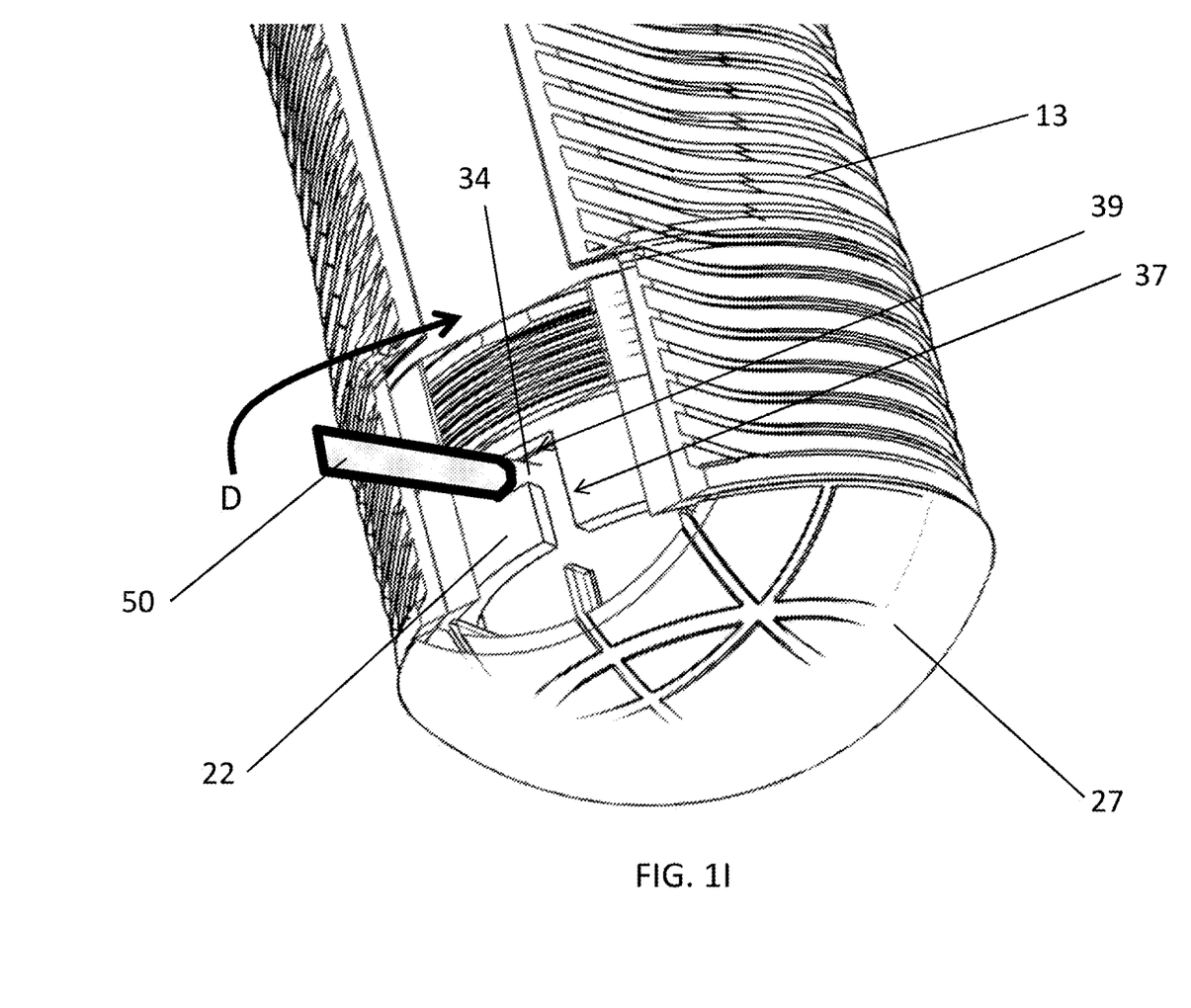

In some embodiments, trigger mechanism 30 further comprises a release lever 50 (Figure II) for releasing spring 18 for use at the same time that interface 16 is pressed against a face of a subject. As shown in Figure II lever 50 is pushed in a direction "D" to move lock pin 34 out of the locked part 39 of L-shaped groove 36 to the point of release of lock pin 34 in the perpendicular unlocked part 37 of L-shaped groove 36 thereby freeing piston 20 from cylinder 22. Release lever 50 may be positioned in any other position on device 10 or may use any other activation means, and the illustrated position and working of release lever 50 should not be considered limiting. In some embodiments, release lever 50 can only be activated when airway interface 16 is firmly positioned over the nose and/or mouth of a subject. Firmly positioned as used herein implies that seal 19 is sufficiently sealed around the nose and/or mouth of the subject such that the vacuum generated by pump 30 is concentrated in the airway of the subject. In some embodiments, spring 18, piston 20 and cylinder 22 are configured to generate a suction force of 200-400 mm Hg at airway interface 16. In some embodiments, due to the use of a spring-loaded piston, such a force is generated in less than one second.

In some embodiments, device 10 further includes a limiter (stop pin or lever) (not shown) for limiting movement of piston 20 (e.g. to a quarter, half, or three quarters of full movement) to thereby control the amount of suction created in cylinder 22. Limiting piston 20 movement can be used, for example, in infants that require a lower suction force.

Reference is now made to FIG. 2 showing an illustrative drawing of use of a device for clearing an airway obstruction according to some embodiments. As shown in FIG. 2, device 10 (such as described above with reference to FIGS. 1A-1I) of the present disclosure can be used to clear an obstructed airway of a subject 200 as follows: Airway interface 16 is pushed over the nose and mouth of subject 200 while optionally supporting the head of subject 200. Device 10 is activated by holding sleeve 13 and pushing on sleeve 13 to push seal 19 of interface 16 against the face of subject 200 thereby releasing piston 20 as described above and generating a suction force in the airway of subject 200 for sucking out the blocking item from the airway of subject 200. Alternatively a release lever 50 is activated to release piston 20.

If a further application of suction is required, piston 20 is pushed against spring 18 to return lock pin 34 to the initial locked position in locked part 39 of L-shaped groove 36. A subsequent suction activation can then be effected by repeating the process as described above.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A device for clearing an obstructed airway of a subject comprising:
    an airway interface configured to be positioned over a mouth and/or nose of the subject;
    a body;
    a pump in fluid communication with the airway interface and configured to generate suction at the airway interface when activated; and
    a sleeve surrounding the pump,
    wherein the device is configured to activate the pump to generate the suction when the airway interface is pushed against the mouth and/or nose of the subject by pushing on the sleeve,
    wherein the device is configured to be held and activated with one hand,
    wherein the pump includes a spring and a piston both mounted in a cylinder,
    wherein the pump is configured such that the spring is compressed when the piston is locked in a closed position and such that unlocking of the piston results in decompression of the spring for the activation of the pump,
    wherein the sleeve surrounds the body,
    wherein the body is connected to the airway interface,
    wherein the pump is mounted in the body,
    wherein the body further includes a slanted groove and the cylinder further includes an L-shaped groove including a locked part for holding a lock pin in a locked position, and
    wherein the device is configured such that movement of the sleeve towards the airway interface moves the slanted groove to thereby drive the lock pin along the slanted groove to thereby move the lock pin into an unlocked part of the L-shaped groove to thereby unlock the piston.

2. The device of claim 1, wherein the sleeve is a grippable sleeve.

3. The device of claim 1, wherein the airway interface includes a seal for sealing around a mouth and/or nose of a subject.

4. The device of claim 1, wherein the sleeve is slidably mounted on the cylinder and configured such that pushing of the sleeve towards the airway interface unlocks the piston.

5. The device of claim 1, wherein pushing the sleeve towards the airway interface, moves the lock pin to thereby unlock the piston.

6. The device of claim 1, wherein a spring constant of the spring is 200-400 N/m.

7. The device of claim 1, wherein a force applied by the spring is 50-90 N.

8. The device of claim 1, wherein the pump is capable of generating a suction force greater than 100 mm Hg within a second or less.

9. The device of claim 1, wherein the pump includes a pneumatic/hydraulic piston.

10. A method of clearing an obstructed airway comprising:
    positioning an airway clearing device over a mouth and/or nose of a subject, the airway clearing device including an airway interface configured to be positioned over a mouth and/or nose of the subject, a body, a pump in fluid communication with the airway interface and configured to generate suction at the airway interface when activated, and a sleeve surrounding the pump, wherein the device is configured to activate the pump to generate the suction when the airway interface is pushed against the mouth and/or nose of the subject by pushing on the sleeve, wherein the device is configured to be held and activated with one hand, wherein the pump includes a spring and a piston both mounted in a cylinder, wherein the pump is configured such that the spring is compressed when the piston is locked in a closed position and such that unlocking of the piston results in decompression of the spring for the activation of the pump, wherein the sleeve surrounds the body, wherein the body is connected to the airway interface, wherein the pump is mounted in the body, wherein the body further includes a slanted groove and the cylinder further includes an L-shaped groove including a locked part for holding a lock pin in a locked position, wherein the device is configured such that movement of the sleeve towards the airway interface moves the slanted groove to thereby drive the lock pin along the slanted groove to thereby move the lock pin into an unlocked part of the L-shaped groove to thereby unlock the piston; and
    pushing the sleeve to thereby push the airway interface against the mouth and/or nose to thereby activate the pump,
    wherein the pushing of the sleeve is performed with one hand.

11. The method of claim 10, wherein the sleeve is a grippable sleeve.

12. The method of claim 10, wherein the airway interface includes a seal for sealing around a mouth and/or nose of a subject.

13. The method of claim 10, wherein the sleeve is slidably mounted on the cylinder and configured such that pushing of the sleeve towards the airway interface unlocks the piston.

14. The method of claim 10, wherein pushing the sleeve towards the airway interface, moves the lock pin to thereby unlock the piston.

* * * * *